United States Patent
Gagnon

(10) Patent No.: US 10,329,322 B2
(45) Date of Patent: Jun. 25, 2019

(54) METHODS FOR REDUCING AGGREGATE CONTENT OF PROTEIN PREPARATIONS BY TREATMENT WITH ARYL ANIONS

(71) Applicant: AGENCY FOR SCIENCE, TECHNOLOGY AND RESEARCH, Singapore (SG)

(72) Inventor: Peter Stanley Gagnon, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 342 days.

(21) Appl. No.: 15/121,655

(22) PCT Filed: Feb. 27, 2014

(86) PCT No.: PCT/SG2014/000085
§ 371 (c)(1),
(2) Date: Aug. 25, 2016

(87) PCT Pub. No.: WO2015/130221
PCT Pub. Date: Sep. 3, 2015

(65) Prior Publication Data
US 2016/0362447 A1  Dec. 15, 2016

(51) Int. Cl.
*C07K 1/14* (2006.01)
*C07K 1/32* (2006.01)
*C07K 1/34* (2006.01)
*C07K 1/36* (2006.01)
*B01D 15/32* (2006.01)
*B01D 15/36* (2006.01)
*B01D 15/38* (2006.01)
*C07K 16/00* (2006.01)

(52) U.S. Cl.
CPC .............. *C07K 1/32* (2013.01); *B01D 15/327* (2013.01); *B01D 15/363* (2013.01); *B01D 15/3828* (2013.01); *C07K 1/145* (2013.01); *C07K 1/34* (2013.01); *C07K 1/36* (2013.01); *C07K 16/00* (2013.01); *B01D 15/36* (2013.01)

(58) Field of Classification Search
CPC . C07K 1/32; C07K 16/00; C07K 1/34; C07K 1/36; B01D 15/327; B01D 15/363; B01D 15/3828

See application file for complete search history.

(56) References Cited

U.S. PATENT DOCUMENTS 5,283,339 A * 2/1994 Arnold ..................... C07K 1/22
548/104
5,883,256 A * 3/1999 Schuler ................. A61L 2/0088
546/102

FOREIGN PATENT DOCUMENTS

WO  2013180648 A1  12/2013
WO  2013180650 A1  12/2013

OTHER PUBLICATIONS

Extended European Search Report dated Nov. 3, 2017, for related European application No. 14883670.3.
Gan et al., "Characterization and removal of aggregates formed by nonspecific interaction of IgM monoclonal antibodies with chromatin catabolites during cell culture production", Journal of Chromatography A 1291, (2013), pp. 33-40.

* cited by examiner

*Primary Examiner* — Vishal V Vasisth
(74) *Attorney, Agent, or Firm* — Pillsbury Winthrop Shaw Pittman LLP

(57) ABSTRACT

A method of reducing the aggregate content in a preparation having a target protein includes contacting the preparation with an aryl anion to form a mixture and contacting the mixture with at least one electropositive solid to remove excess aryl anion.

12 Claims, No Drawings

METHODS FOR REDUCING AGGREGATE CONTENT OF PROTEIN PREPARATIONS BY TREATMENT WITH ARYL ANIONS

RELATED APPLICATIONS

This application is a U.S. National Stage of International Patent Application No. PCT/SG2014/000085, filed Feb. 27, 2014, entitled METHODS FOR REDUCING AGGREGATE CONTENT OF PROTEIN PREPARATIONS BY TREATMENT WITH ARYL ANIONS, and naming inventor Peter Stanley Gagnon, which published as International Patent Publication No. WO/2015/130221 on Sep. 3, 2015. The entire content of the foregoing application is incorporated herein by reference, including all text, tables and drawings.

BACKGROUND

Embodiments disclosed herein relate to methods for enhancing purification of proteins, including antibodies. They particularly relate to methods for reducing the level of aggregates and can be combined with methods of cell culture harvest clarification. They further relate to integration of these capabilities with other purification methods to achieve a desired level of protein purity.

Aggregate removal is an important aspect of protein purification. It has been shown that low concentrations of the yellow fluorescent heterocyclic dye ethacridine reduces aggregate content of antibody preparations, and that this result may be the result of chromatin removal (Gan et al J. Chromatography A 1291 (2013) 33-40). Ethacridine has a long history as a protein precipitating agent.

The aryl anionic dye Methyl Blue is used for histological staining and has been used to mediate electron transfer in microbial fuel cells. Methyl blue is also known by the names Cotton Blue, Helvetia Blue, and Acid Blue 93. The reagent has not been employed in the field of protein fractionation.

SUMMARY

In some aspects, embodiments disclosed herein relate to methods of reducing the aggregate content in a preparation comprising a target protein, the method comprising contacting the preparation with an aryl anion to form a mixture, and contacting the mixture with at least one electropositive solid to remove excess aryl anion.

DETAILED DESCRIPTION

Embodiments disclosed herein provide methods for reducing the amount of aggregates in a sample containing a desired protein, such as a protein preparation, by treating the preparation with aryl anions. In certain embodiments, the reduction of complexes and/or aggregates is achieved with low levels of aryl anions. In certain embodiments, the sample is treated at elevated conductivity values (salt concentration). In certain embodiments, the treated sample is subsequently exposed to solid materials bearing chemical moieties that selectively remove aryl anions and aggregates from the protein preparation.

Methods and kits are provided for the purification of proteins. In some embodiments, the disclosed methods provide for the reduction of aggregates from preparations of antibodies or other proteins through the contact of such desired protein with one or more species of aryl anion. In certain embodiments, the disclosed methods may be practiced at a range of conductivity levels from so-called physiological conditions to conductivity values up to 3 or more times higher than such conditions. Such elevated conductivity levels may permit the method to be applied to acidic proteins without risking their precipitation during treatment, and thereby increase the diversity of desired protein species to which the disclosed methods may be applied. In certain embodiments, the disclosed methods may be practiced with low concentrations of the aryl anions; such as 0.1% to 1.0%. The disclosed methods provide in certain embodiments contacting the treated protein preparation with solid materials that enhance the overall ability of the treatment to reduce aggregate content, usually in parallel with reducing host protein contamination, and provide the additional advantage of removing excess aryl anions. In certain embodiments, the aryl anion is methyl blue.

In certain embodiments, the disclosed methods provide for reducing levels of aggregates which have high molecular weight in comparison with the desired protein, such as homo-aggregates, and also for reducing levels of aggregates of hydrodynamic size only modestly greater than the desired protein, such as hetero-aggregates. In certain embodiments, aggregates comprise hetero-aggregates of the desired protein and a contaminant and in certain such embodiments the contaminant is a nucleic acid, nucleotide, endotoxin, metal ion, protein, lipid, or cell culture media component. In certain embodiments, the presence of homo-aggregates of the desired protein is substantially eliminated. In certain embodiments, the presence of hetero-aggregates of the desired protein and a contaminant is substantially eliminated. In certain embodiments, the presence of homo- and hetero-aggregates not including the desired protein are substantially eliminated.

In certain embodiments, the disclosed methods additionally provide for the reduction of contaminants such as DNA, endotoxin, and virus levels along with reduction of aggregates. In certain embodiments the disclosed methods is practiced with the additional inclusion of antiviral agents beyond the aryl anion itself.

In certain embodiments, the protein species of interest (e.g., the desired protein to be purified) is of recombinant origin, and the protein preparation may include a cell-containing cell culture harvest, a cell culture supernatant, clarified cell culture supernatant, an eluate from a chromatography column, or protein-containing solution obtained from a previous stage of purification. In certain embodiments, the protein preparation contains an antibody and in certain of such embodiments the antibody is an IgG, an IgM, or a fragmentary form thereof, or a fusion protein of an antibody or antibody fragment, such as an Fc-fusion protein. In certain embodiments, the desired protein may be a clotting protein, such as Factor VIII. In certain embodiments, the desired protein may be a peptide hormone, such as human growth hormone.

In certain embodiments, the disclosed methods are practiced such that the conductivity of the sample is at a sufficiently high level to substantially avoid precipitation of the desired protein from the sample. Conductivity may be adjusted by addition of salts or diluents according to methods known in the art. In certain embodiments, the conductivity is 5 mS/cm, 10 mS/cm, 15 mS/cm or 20 mS/cm greater than the level determined to be needed to avoid substantial precipitation of the desired protein. In certain embodiments the conductivity is in a range generally considered to correspond to physiological conductivity, such a 12-17 mS/cm. In certain embodiments, the conductivity is greater than 20 mS/cm, 25 mS/cm, 30 mS/cm, 35 mS/cm, 40 mS/cm, 45 ms/cm or greater than 45 mS/cm. The ability of the method to remove important subsets of contaminants at elevated conductivities represents one of the surprising features of the disclosed methods, since charge interactions in these system are known to be reduced at elevated conductivities. In certain embodiments, the operating pH may be neutral to slightly alkaline and still have sufficient utility for removing chromatin. In some embodiments, the operating pH may be acidic, such as including values of 6 or 5 or 4, and as a result of lower pH may be more effective for removal of non-histone proteins. In such embodiments, it may also be useful to reduce the conductivity.

In certain embodiments, the aryl anion is methyl blue. In related embodiments, the aryl anion may be an aryl anion other than methyl blue.

In certain embodiments, the aryl anion is provided at substantially the lowest concentration sufficient to promote the desired degree of reduction of aggregates. In certain embodiments, the concentration of the aryl anion may be less than (on a weight per volume basis) 5%, 1%, 0.5%, 0.1%, 0.05%. In certain embodiments the aryl anion is provided in concentrations of 0.1-1.0%, or 0.2-0.8%, or 0.04-0.06%.

In certain embodiments, the disclosed methods may be practiced an operating pH of 4-7, or 4.5-6.0, or 5.0 to 5.5, or 5.1 to 5.3, or 5.15 to 5.25, or an intermediate value In certain embodiments, the sample is additionally contacted with an antiviral agent such as tri (n-butyl) phosphate. Such antiviral agents may be present in an amount less than approximately 1% (w/v), less than approximately 0.1% (w/v), or less than approximately 0.01% (w/v) or less than approximately 0.001%.

In certain embodiments, the method additionally includes the step of contacting the sample with a ureide in an amount sufficient for the ureide to be undissolved in the sample. The supernatant containing the desired protein can then be separated from the balance of the sample including precipitated contaminants. In certain of such embodiments the ureide is supplied prior to the step of contacting the sample with the aryl anion, in others the ureide is supplied substantially simultaneously with the step of contacting the sample with the aryl anion, and in yet others the ureide is supplied after the step of contacting the sample with the aryl anion. In certain such embodiments, the ureide can be any of uric acid, hydantoin (imidazolidine-2,4-dione), allantoin (2,5-Dioxo-4-imidazolidinyl) urea, alcloxa, aldioxa, hemocane, ureidohydantoin, 5-ureidohydantoin), glyoxylureide, glyoxylic acid diureide, 2,5-dioxo-4-imidazolidinyl urea (allantoin), imidazolydinyl urea, diimidazolydinyl urea, and a purine. In certain embodiments the ureide is allantoin and in some such cases the allantoin is present in concentrations greater than 0.56% (w/v), 1%, 1.5%, 2%, or greater. In certain embodiments the ureide is uric acid and in some such cases the uric acid is present in concentrations greater than 0.0025% (w/v), 0.005%, 0.01%, 0.05%, 0.1%, 1% or greater.

In certain embodiments, the method additionally includes the step of contacting the sample with a ureide in an amount where the ureide is fully dissolved. In certain such embodiments, the soluble ureide can be urea, imidazolydinal urea, or another ureide. In certain embodiments the ureide is urea and in some such cases the urea is present in concentrations greater than 0.5 M, or greater than 1 M, or greater than 2 M, or greater than 4 M, or than 6 M, or greater than 8 M. This emphasizes again the surprising nature of the method, where avoidance of precipitation is a particular object of the method. Highly soluble ureides such as urea have the general effect of increasing the solubility of many compounds, which is to say their presence opposes the formation of precipitates.

In certain embodiments, the utility of the disclosed methods is enhanced by the fact that they also accelerate sedimentation of cell debris in cell culture harvests, and substantially reduces levels of DNA, endotoxin, and virus, when present. Experimental data suggest that the ability of some ureides to preferentially interact with aggregates, endotoxin, and virus contribute to these results, and that low levels of dissolved ureides may contribute to the higher antibody recovery they support in comparison to treatment with multivalent anions in the absence of ureides. Following treatment, solid materials may be removed by sedimentation or filtration, leaving the substantially aggregate-free protein in the supernatant.

In certain embodiments, the disclosed methods may be practiced with the additional step of contacting the sample with a soluble organic modulator such as a nonionic organic polymer, organic solvent, surfactant, or ureide. In certain of such embodiments the step of contacting the sample with the organic modulator occurs prior to the step of contacting the sample with the aryl anion. In others, the step of contacting the sample with the organic modulator occurs substantially simultaneously with the step of contacting the sample with the aryl anion. In yet others, the step of contacting the sample with the organic modulator occurs after the step of contacting the sample with the aryl anion. In certain embodiments, the organic modulator is a nonionic organic polymer such as polyethylene glycol, polypropylene glycol and polybutylene glycol and in certain of such embodiments the nonionic organic polymer has an average molecular weight of approximately 1000 D or less, 500 D or less, 250 D or less, or 100 D or less. In certain embodiments, the organic modulator is an organic solvent such as ethylene glycol, propylene glycol, butylene glycol, dimethylsulfoxide, ethanol, or phenoxyethanol. In certain embodiments, the organic modulator is provided at a concentration of approximately 1% (w/v) or greater. In certain embodiments, the organic modulator is a surfactant such as Tween, triton, CHAPS, CHAPSO or octyl glucoside and in certain of such embodiments the surfactant is provided at a concentration of approximately 1% (w/v) or less, approximately 0.1% or less or approximately 0.02% (w/v) or less. In certain embodiments, the organic modulator is a ureide provided in a subsaturating amount and in certain of such embodiments the ureide is urea, hydantoin, or allantoin.

In certain embodiments, the disclosed methods provide for a kit for the convenient practice of certain methods of the disclosed methods. Such kit may provide reagents useful for the practice of the disclosed methods such one or more aryl anions, ureides, organic modulators, antiviral agents, and reagents for the adjustment of conductivity. The kit may provide materials in amounts and concentrations adapted to the practice of the disclosed methods for use in the purification of proteins. Such kits may be adapted for use with certain proteins such as IgG or IgM antibodies and may be adapted to quantities suitable for certain scales of protein preparation and purification.

In certain embodiments, the disclosed methods may be followed by contact of the sample with solid materials with the intent of the solids having the effect of selectively removing the excess aryl anions or other sample components from the sample prior to additional processing.

In certain embodiments, the disclosed methods may be combined with conventional protein purification methods to achieve higher levels of purification or to remove other contaminants. For example, the disclosed methods may be practiced in preparation for conventional purification methods involving precipitation, chromatography, and liquid-liquid extraction methods. It is within the ability of a person of ordinary skill in the art to develop appropriate conditions for these methods and integrate them with the disclosed methods described herein to achieve the desired purification of a product.

In certain embodiments, operating conditions may be varied with respect to pH, and/or by the presence of chelating agents, organic polymers or solvents, surfactants, chaotropes, and various species of salts in order to modulate the degree to which aggregates are reduced and the desired protein remains in solution.

In some embodiments, there are provided methods of reducing the aggregate content in a preparation comprising a target protein, the method comprising contacting the preparation with an aryl anion to form a mixture, and contacting the mixture with at least one electropositive solid to remove excess aryl anion.

In some embodiments, methods disclosed herein further comprise contacting the mixture, simultaneously or sequentially, with at least one additional electropositive solid.

In some embodiments, methods disclosed herein further comprise contacting the mixture with supersaturated allantoin.

In some embodiments, allantoin is present in a concentration range selected from the group consisting of: (a) from about 0.6 to about 50%; (b) from about 1 to about 10%; and (c) from about 1 to about 2%.

In some embodiments, the aryl anion is methyl blue.

In some embodiments, the aryl anion is present in a concentration range selected from the group consisting of: (a) from about 0.1% to about 0.5%; (b) from about 0.02 to about 0.4%, and (c) from about 0.25 to about 0.3%.

In some embodiments, an operating conductivity is in a range selected from the group consisting of: (a) from about 0.1 to about 50 mS/cm; (b) from about 1 to about 30 mS/cm; and (c) from about 5 to about 15 mS/cm.

In some embodiments, an operating pH is in a range selected from the group consisting of: (a) from about 3 to about 8, (b) from about 4 to about 7; (c) from about 5 to about 6; (d) from about 4.5 to 5.5; (e) from about 5.1 to about 5.3.

In some embodiments, the mixture further comprises antiviral agent tri(n-butyl)phosphate.

In some embodiments, a surface of the at least one electropositive solid promotes a chemical interaction selected from the group consisting of electrostatic interactions, hydrophobic interactions, hydrogen bonding, and metal affinity.

In some embodiments, the at least one electropositive solid is particulate.

In some embodiments, the target protein comprises one selected from the group consisting of a recombinant protein, an antibody, a growth hormone, and a clotting factor.

In some embodiments, the preparation is one selected from the group consisting of a cell-containing cell culture harvest, a substantially cell-free cell culture harvest, and a partially purified protein.

In some embodiments, there are provided kits for the convenient practice of the methods disclosed herein. Such kits may include one or more of the necessary reagents for carrying out the methods, along with instructions for practicing the methods.

Terms are defined so that the disclosed methods may be understood more readily. Additional definitions are set forth throughout the detailed description.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homoaggregates" refers to a stable association of two or more proteins of identical composition; "Heteroaggregates" refers to a stable association of one or more proteins of identical or different composition, optionally associated with one or more non-protein molecules. The non-protein component may consist of one more entities from the group consisting of a nucleotide, an endotoxin, a metal ion, a lipid, or a cell culture media component.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

"Endotoxin" refers to a toxic heat-stable lipopolysaccharide substance present in the outer membrane of gram-negative bacteria that is released from the cell upon lysis.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the disclosed methods include but are not limited to polyethylene glycol (PEG), polypropylene glycol, and polyvinylpyrrolidone (PVP). PEG has a structural formula HO—(CH$_2$—CH$_2$—O)$_n$—H. Examples include, but are not limited to compositions with an average polymer molecular weight ranging from less than 100 to more than 1000 daltons.

"Aryl anion" refers to an organic structure consisting of at least one ring, at least one negative charge, a net negative charge, and an optional absence of positive charges. For example, an aryl anion may bear no positive charges. If the aryl anion bears a positive charge, it may bear at least two negative charges. If it bears two positive charges, it may bear at least 3 negative charges, and so on "Organic solvent" refers to naturally occurring or synthetic organic compound existing in a liquid state. Examples suitable to practice the disclosed methods include but are not limited to ethylene glycol, propylene glycol, dimethyl sulfoxide, ethanol, and phenoxyethanol.

"Organic polymer" refers to a naturally occurring synthetic polymer of an organic monomer. Examples include but are not limited to polyethylene glycol, polypropylene glycol, dextran, or cellulose, among others.

"Polynucleotide" refers to a biopolymer composed of multiple nucleotide monomers covalently bonded in a chain. DNA (deoxyribonucleic acid) and RNA (ribonucleic acid) are examples of polynucleotides.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Undissolved ureide" refers to a solution containing an amount of ureide in excess of its maximum solubility under the conditions prevailing in a particular protein preparation. In certain embodiments, the disclosed methods provides a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the disclosed methods include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3, 3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl) dimethylammonio]-2-hydroxy-1-propanesulfonate), and octyl glucoside (e.g., (2R,3S,4S,5R, 6R)-2-(hydroxymethyl)-6-octoxyoxane-3,4,5-triol).

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

In the course of evaluation of aryl anions for use in certain embodiments, the conditions for application may be investigated as follows. The use of aryl anions potentially imposes some restrictions on the conditions that may be used to practice the method in certain embodiments. For example, it can be desirable to employ conditions that substantially prevent strong interactions between the aryl anions and the protein of interest. A simple method to obtain an approximation of such conditions is to apply the protein of interest to an anion exchanger and elute it in a salt gradient. A salt concentration just above the threshold at which the protein elutes roughly identifies the minimum conductivity at which the method may be most effectively practiced. This concentration will be influenced by pH, which can be modeled by the same means. Given that the method is applied to a cell culture supernatant, an IgG antibody may employ the addition of salt or modification of pH to avoid significant losses. IgM antibodies and non-antibody proteins may employ the addition of higher concentrations of salt, even sufficient to create conductivity values approaching 30 mS/cm (about 2 times higher than physiological).

In certain embodiments, one effective means of evaluating conditions for clarified cell culture supernatants containing IgG monoclonal antibodies is to cover a range of 0.3 to 0.7% aryl anions, and conductivities ranging from half-physiological to 2 times physiological. The ranges can be extended further if results indicate it may be helpful to do so, or narrowed and evaluated at finer increments.

In certain embodiments, a convenient starting point for developing a purification procedure according to the disclosed methods for clarified cell culture supernatants is to use 0.1% methyl blue.

In certain embodiments, it may be advantageous to begin by dispersing an organic modulator in the protein preparation before adding the aryl anion, since that practice may improve antibody recovery. Long incubation before addition of the aryl anion appears to be unnecessary; 15 minutes or less is adequate, although there appears to be no disadvantage to longer incubation. Experimental data generally indicate that addition of allantoin in a supersaturating amount of about 1% increases the recovery of IgG.

In certain embodiments, it is recommended that the aryl anions anion be dissolved, for example in water or buffer, prior to its addition to the sample, to facilitate their rapid distribution throughout the protein preparation. Care should be taken to avoid persistent local excesses, for example by gradually infusing the dissolved aryl anions into a well-mixing suspension. Incubation time should be at least 15 minutes, better 60-120 minutes, but appears not to benefit significantly from durations greater than 120 minutes.

The method may generally be practiced at ambient temperature but may be conducted at higher or lower temperatures, for example ranging from 4° to 37° C. Experimental data indicate that the temperature does not substantially alter the obtained results, which will leave the stability requirements of the protein as an important factor in selection of operating temperature.

In certain embodiments, the aryl anion is dissolved or dispersed, for example in water or buffer, and the pH adjusted prior to its addition to the sample. This is because certain preparations of aryl anions, such as free-acid forms, are acidic and have the potential to substantially alter the experimental conditions in an unintended manner.

In certain embodiments involving the use of both superstaturated ureides and aryl anions, it may generally be advantageous to begin by dispersing the ureide in the protein preparation before adding the aryl anions, since experience with the ureide allantoin indicates that this practice can improve antibody recovery. Long incubation before addition of the aryl anion appears to be unnecessary; 15 minutes or less is adequate, although there appears to be no disadvantage to longer incubation.

Multiple options exist for monitoring the aggregate dissociation or removal achieved by the method, whether during method development or manufacturing. The simplest is to conduct analytical size exclusion chromatography on a column with suitable selectivity and monitor at a UV wavelength of 280 nm. This may reveal HMW (high molecular weight) aggregates, since they usually embody hydrodynamic dimension that reasonably conform to multiples of the size of the non-aggregated product. Hetero-aggregates are commonly overlooked by this method since their hydrodynamic dimensions may be only modestly greater than those of the non-aggregated product. In such cases, the heteromorphic composition of the aggregate may be revealed by calculating the ratio of UV absorbance at 254 nm to absorbance at 280 nm, then comparing that value against the absorbance ratio for purified protein that is believed to be totally free of associated contaminants. Hetero-aggregates containing DNA, for example, will be revealed by an elevated ratio of 254/280.

In certain embodiments, the disclosed methods can be integrated with treatment to remove the aryl anions and potentially other components of the sample prior to subsequent purification. Such treatments may include exposure of the sample to solids bearing chemical moieties that are complementary in their nature to the characteristics of the aryl anions with the goal that they sequester the aryl anions from the remainder of the sample. Since aryl anions are understood to be negatively charged and hydrophobic, it follows that positively charged surfaces, including hydrophobic positively charged surfaces, should be especially useful for sequestering excess aryl anions. Solids of other surface composition may be included to sequester other components of the sample.

In certain embodiments, the disclosed methods can be integrated with one or more purification methods, including but not limited to protein A and other forms of biological affinity chromatography, anion exchange chromatography, anion exchange chromatography, hydrophobic interaction chromatography, immobilized metal affinity chromatography, hydroxyapatite or other mixed mode chromatography, and/or non-chromatographic methods such as precipitation and liquid-liquid extraction. It is within the purview of a person of ordinary skill in the art to develop appropriate conditions for the various methods and integrate them with the disclosed methods herein to achieve the necessary purification of a particular antibody.

EXAMPLES

Example 1

An experiment was conducted to determine the dynamic range of methyl blue at pH 5.2 and physiological conductivity. The sample was a cell culture harvest containing about 1 g/L IgG antibody, 310,010 ppm host proteins, and 10.5% aggregates. In separate experiments, methyl blue was added to final amounts of 0.01; 0.05, 0.1 and 0.5%. The mixtures were incubated for 2 hours, and samples were drawn for analysis. Antibody recovery was 106%, 62%, 21%, and 0%. Host protein content was 239,175 ppm, 246,497 ppm, 714,356 ppm, 0 ppm. Aggregate content was 8.6%, 4.4%, 14.6%, 21.8%. The increase in host protein and aggregates at the higher methyl blue concentrations was judged to reflect the loss of IgG.

Example 2

The four treated samples from example one were further treated by exposure to electropositive metal affinity particles in the form of TREN 40 high (Bio-Works), in an amount of 5% v/v. Recovery of IgG across the 2 steps (example 1 treatment+example 2 treatment) was 90%, 91%, 87%, 0%. Aggregates were reduced to less than 1%, less than 2%, less than 2%, and unmeasurable (not detected). Host cell proteins were reduced to about 140,000 ppm; about 177,000 ppm; about 60,000 ppm, and an unmeasurable number (not detected). These results are unexpected because recovery values are mostly increased as a result of the particle contact step, and because they reveal a surprising synergistic effect.

Example 3

An IgG-containing cell culture was treated by addition of allantoin to a concentration of 1%, then the pH was reduced to 5.2, and methyl blue was added to a final amount of 0.1%. The mixture was incubated for 2 hours then TREN particles as described in example 3 were added to a final amount of 5% v/v, and incubated mixing for an additional 4 hours. Solids were removed by centrifugation, the pH was titrated to 7, and the liquid was passed through a PCI electropostive depth filter (Sartorius). IgG recovery was 84%. Aggregates were reduced from an original 13.4% to 0.4%. Host proteins were reduced from an original 234, 557 ppm to 47,746 ppm.

It will be understood by the person of ordinary skill in the art how to scale up or scale down the results from experiments such as those described in the above examples, to whatever volume required to meet their, particular requirements.

All references cited herein are incorporated by reference in their entirety and for all purposes, to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present disclosed methods.

Many modifications and variations of the disclosed methods can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the disclosed methods being indicated by the following claims.

The invention claimed is:

1. A method of reducing the aggregate content in a preparation comprising a target protein, the method comprising:
   (a) contacting the preparation with methyl blue to form a mixture;
   (b) contacting the mixture with at least one electropositive solid to remove excess methyl blue; and
   (c) separating the target protein from the electropositive solid.

2. The method of claim 1, further comprising contacting the mixture with at least one additional electropositive solid.

3. The method of claim 1, wherein the methyl blue is present in a concentration range of about 0.02 to about 0.4%.

4. The method of claim 1, wherein an operating conductivity is in a range of about 0.1 to about 50 mS/cm.

5. The method of claim 1, wherein an operating pH is in a range of about 3 to about 8.

6. The method of claim 1, wherein the mixture further comprises antiviral agent tri(n-butyl)phosphate.

7. The method of claim 1, wherein the at least one electropositive solid is particulate.

8. The method of claim 1, wherein the target protein comprises one selected from the group consisting of a recombinant protein, an antibody, a growth hormone, and a clotting factor.

9. The method of claim 1, wherein the preparation is one selected from the group consisting of a cell-containing cell culture harvest, a substantially cell-free cell culture harvest, and a partially purified protein.

10. A method of reducing the aggregate content in a preparation comprising a soluble target protein, the method comprising:
  (a) contacting the preparation with methyl blue to form a mixture, wherein the methyl blue is present at a concentration from about 0.01% to about 0.1%;
  (b) contacting the mixture with an electropositive solid; and
  (c) separating the soluble target protein from the electropositive solid.

11. The method of claim 10, wherein the soluble target protein comprises an antibody.

12. The method of claim 7 or 10, wherein the electropositive solid comprises tris(2-aminoethyl)amine (TREN).

* * * * *